(12) United States Patent
Samsoondar et al.

(10) Patent No.: US 6,582,964 B1
(45) Date of Patent: Jun. 24, 2003

(54) METHOD AND APPARATUS FOR RAPID MEASUREMENT OF $HBA_{1C}$

(75) Inventors: James Samsoondar, Cambridge (CA); Romuald Pawluczyk, Conestogo (CA); Petersen Borge, Elimira (CA); Theordore E. Cadell, Conestogo (CA); Bernard Zinman, Toronto (CA); Bronislaw Bednarz, Toronto (CA)

(73) Assignee: CME Telemetrix Inc., Waterloo (CA)

( * ) Notice: Subject to any disclaimer, the term of this patent is extended or adjusted under 35 U.S.C. 154(b) by 0 days.

(21) Appl. No.: 09/958,933

(22) PCT Filed: May 11, 2000

(86) PCT No.: PCT/CA00/00549

§ 371 (c)(1),
(2), (4) Date: Jan. 23, 2002

(87) PCT Pub. No.: WO00/70350

PCT Pub. Date: Nov. 23, 2000

Related U.S. Application Data

(60) Provisional application No. 60/133,876, filed on May 12, 1999.

(51) Int. Cl.[7] ................................ G01N 33/72
(52) U.S. Cl. ................ 436/67; 436/66; 436/164; 436/171; 422/82.05; 422/82.09
(58) Field of Search .............. 436/63, 66, 67, 436/164, 171; 422/82.05, 82.09

(56) References Cited

U.S. PATENT DOCUMENTS 6,177,283 B1 * 1/2001 Ray ........................ 436/530

FOREIGN PATENT DOCUMENTS

| EP | 222419 | * | 5/1987 |
| EP | 0598329 | | 5/1994 |
| EP | 0631137 | | 12/1994 |
| EP | 881495 | * | 12/1998 |
| WO | 98/39634 | * | 9/1998 |

OTHER PUBLICATIONS

"Sigma Biochemikalien und reagenzien fur die Naturwissenschaftliche Forschung", 1997, Sigma Chemical Co., Germany XP002146316, see "Probe –clip press–seal incubation chambers", p. 2338.

"Katalog Merk, Verbrauchsmaterialien und Geräte", Jan. 1999, Merk Eurolab GMBH, Darmstadt, Germany XP002146317, see "Zylindrische Kuvetten", p. 634.9

* cited by examiner

Primary Examiner—Maureen M. Wallenhorst
(74) Attorney, Agent, or Firm—Katten Muchin Zavis Rosenman

(57) ABSTRACT

Described is a method and apparatus for determining a diabetic patient's compliance with their insulin dosing regime. The method and apparatus involves taking a blood sample from a patient by a routine finger prick and placing it in a special sample tab which is placed in a spectrophotometer sample housing. The spectrophotometer measures Hb and $HbA_{1c}$ concentrations and allows for calculating a ratio of $HbA_{1c}$ to Hb which is indicative of the degree of patient compliance.

28 Claims, 2 Drawing Sheets

METHOD AND APPARATUS FOR RAPID MEASUREMENT OF HBA$_{1C}$

This application claims priority to International Application No. PCT/CA00/00549 filed May 11, 2000, which in turn claims priority to U.S. Provisional Application No. 60/133,876, filed May 12, 1999.

FIELD OF INVENTION

This invention relates to a sample tab and sample housing for performing rapid spectrophotometric measurement of Hemoglobin A$_{1c}$ (HbA$_{1c}$) in whole blood, without the use of any reagent.

BACKGROUND OF INVENTION

Diabetes mellitus is due to absolute or relative insulin deficiency. The most common forms of diabetes are Type 1 or Insulin-dependent diabetes, and Type 2 or Non-insulin-dependent diabetes. What all forms of diabetes have in common is elevation in blood glucose or hyperglycemia. There are about 16 million diabetics in the US, with about 10–15% being Type 1 and the rest being Type 2. Type 1 diabetes is caused by an absolute insulin deficiency, and usually occurs before the age of 30, although it can occur at any age. Consequently, it was also referred to as juvenile diabetes. It is not associated with obesity and is commonly complicated by ketoacidosis. Ketoacidosis is an acute complication of diabetes, and may present as a medical emergency because of dehydration and acidosis (low blood pH). Type 2 diabetes usually develops after the age of 30 and is not associated with total loss of the ability to secrete insulin. Consequently, it was referred to as maturity-onset diabetes. Plasma insulin levels are often normal or elevated. Al most all the patients are obese, and their glucose tolerance may be restored to normal if they loose weight. They have a reduced number of insulin receptors, and the number of these receptors can increase with weight loss. Due to the presence of circulating insulin, ketoacidosis is a rare complication.

The late complications of all forms of diabetes are kidney failure (nephropathy), blindness (due to retinopathy), sensory deficits (due to neuropathy). Recent long-term clinical evaluations report that failure of a patient to maintain glucose levels as close to normal as possible can contribute to these significant complications of diabetes. To adequately control the glucose levels in their blood, diabetic patients must inject themselves with insulin once or twice daily, and must monitor their blood glucose levels between 1 and 4 times daily. The most common method used by diabetic patients for monitoring blood glucose, is to acquire a small sample of blood by sticking the finger with a lancet, and squeezing a droplet of blood onto a paper strip which is then placed on a detection device. The glucose results assist the patients in planing meals and physical activities, and also assist the doctors in optimizing the patients' insulin dosage. Unfortunately, many diabetic patients are not compliant in measuring their blood glucose regularly, and regulating their diet and physical activities, but yet their glucose levels may be at acceptable levels during their visit to the doctor's office. To get around this problem in detecting non-compliance, doctors monitor their patients' HbA$_{1c}$ levels every 2 to 4 months.

HbA$_{1c}$ is one specific type of glycated Hb, constituting approx. 80% of all glycated Hb and is formed by the spontaneous reaction of glucose with the N-terminal amino group of the Hb A beta chain. The HbA$_{1c}$ and the glycated Hb values have a high degree of correlation, and either may be used in the management of diabetes. As a matter of fact, some in vitro diagnostic systems measure glycated Hb but report HbA$_{1c}$ results. Formation of HbA$_{1c}$ irreversible, and the blood level depends on both the life span of the red blood cells (average 120 days) and the blood glucose concentration. Therefore HbA$_{1c}$ represents the time-averaged blood glucose values over the preceding 4 to 6 weeks, and is not subject to the wide fluctuations observed in blood glucose values. Studies have shown that quality of life improves with decreasing levels of HBA$_{1c}$, and measurements every 2 to 4 months are recommended.

The gold standard for measuring HbA1c uses high performance liquid chromatography (HPLC). Other methods use affinity chromatography, ion-exchange chromatography and immunoinhibition turbidimetric techniques. In all the available methods, the first step is the production of a hemolysate by lysing the red blood cells with a special reagent. Since no near-patient testing for HbA$_{1c}$ is currently available, diabetic patients have to visit their doctor a second time to discuss their HbA$_{1c}$ results. The inconvenience to patients and the extra cost for a follow-up visit to the doctor, prompted manufacturers to develop a kit, which enables the patient to place their blood on a specially-treated test strip, which is then sent to a laboratory in a prepaid mailer. Within 1 to 2 weeks, both patients and their doctors receive the HbA$_{1c}$ results. By mailing in a blood sample ahead of time, the follow-up visit to the doctor can be eliminated. A rapid method for performing the HbA$_{1c}$ test in the doctors office is still preferred.

SUMMARY OF THE INVENTION

It is desirable to provide an apparatus and a method whereby a doctor can test his/her patent's HbA$_{1c}$ within minutes. It is preferred that the sample requirement is a drop of blood drawn by finger prick, in a manner comparable to near-patient glucose testing. The advantages of the present invention are the rapid turn-around time during a patient's visit with his/her doctor, and the decreased costs due to absence of reagents.

In its broad aspect the present invention provides an apparatus for determining the concentration of HbA$_{1c}$ and Hb in a blood specimen where the apparatus comprises: a sample tab; a sample housing for receiving a sample; and a radiation source and radiation detector, operatively coupled with a means for providing a determination of glucose concentration in the blood sample based on the absorbed radiation.

According to one embodiment of the present invention, the sample housing comprises a block with a slit for inserting the sample tab, and more preferably, the sample tab consists of a slide or base plate with a depression or well in the base plate for containing the sample and a coverslip which closes when the tab is inserted in the housing, preferably, the cover closes automatically when inserted in the sample housing.

In a preferred embodiment of the present invention, the sample well contains two grooves and an overflow ring for collecting excess blood as it is squeezed out by the closing coverslip. Preferably, the coverslip is attached to the tab so that the blood proximate the coverslip hinge makes contact with the coverslip first; as the coverslip closes, excess blood is squeezed out through the two grooves and into the overflow ring.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

The present invention provides a method of determining a diabetic patient's compliance with their insulin dosing regime comprising quantifying the amount of $HbA_{1c}$ and Hb contained in a blood specimen taken from the patient, without further treatment of the specimen, using a spectrophotometer, and comparing the concentration of $HbA_{1c}$ and Hb, where an elevated ratio of $HbA_{1c}$ reflects a lack of patient compliance.

According to a preferred embodiment of the method of this invention, the method of quantification comprises the steps of:

(i) generating a calibration algorithm for each of the $HbA_{1c}$ and Hb;

(ii) measuring with the spectrophotometer, absorbance of radiation by each of the $HbA_{1c}$ and Hb in the specimen; and (iii) incorporating the absorbances measured in step (ii) in the algorithms respectively and calculating the concentration of the $HbA_{1c}$ and Hb in the specimen.

More preferably, according to the method of the present invention, quantification includes calculation of the first derivatives of at least two portions of a spectrum generated from a scan for each of $HbA_{1c}$ and Hb which are used to calculate each of the $HbA_{1c}$ and Hb concentrations.

According to another aspect of the present invention, the methods can be used with reflectance instead of absorbance.

According to a preferred aspect of the present invention, the method is carried out with a blood specimen being placed into a sample tab comprising a well in which the specimen resides and a cover which closes over the well.

Furthermore, the method provides for the situation where the sample tab well allows for overflow of excess specimen from the well whenever the cover is closed over the well.

Figure 1:
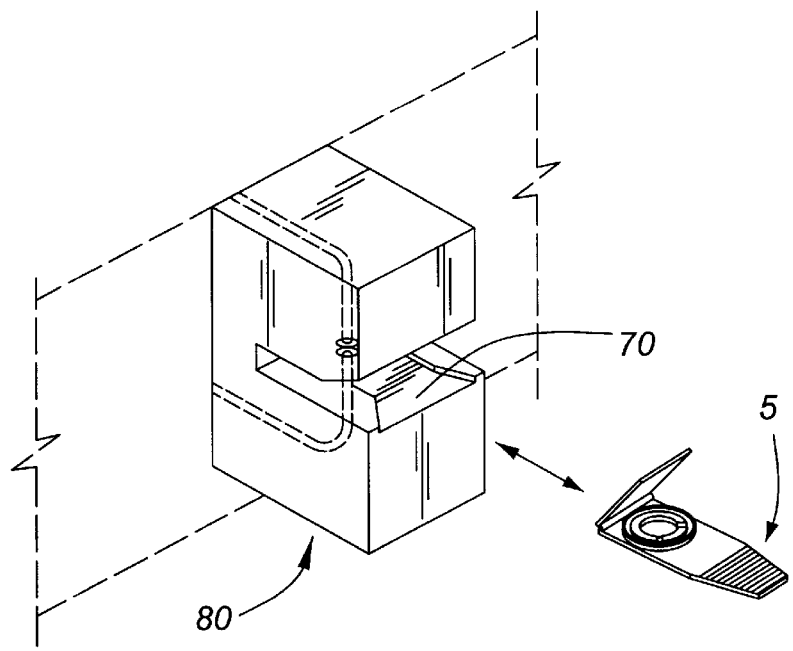
FIG. 1 is a perspective view of a system incorporating an apparatus of the present invention for measuring Hemoglobin A1c.
Figure 1A:
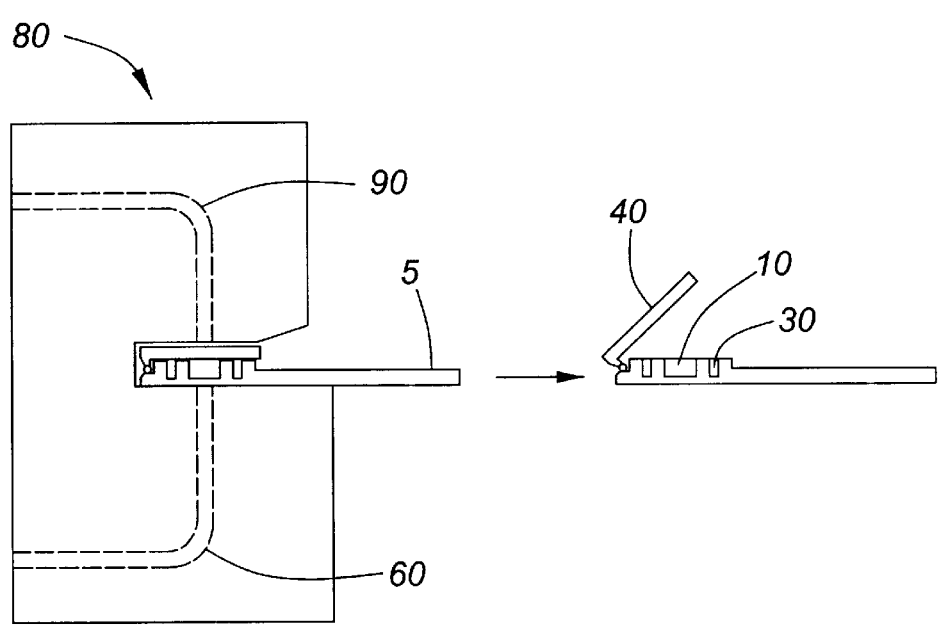

Turning now to the sample housing and sample tab, as may be seen in FIG. 1 the radiation from the spectrophotometer is delivered to the sample in he sample tab through a source or incident optical fibre (60) while the sample rests in a sample tab holder (70) within a sample housing (80). The radiation passing through the sample tab and specimen is received by a receiving optical fiber (90), and processed further to determine concentrations of Hb and $HbA_{1c}$.

Spectrophotometer

A spectrophotometer of the present invention is one with appropriate filters, a grating and a linear photodiode array (PDA) detector; a means for optically connecting the radiation source with the detector along a sample path through the housing and along a reference path which by-passes the sample; a means for selectively passing a beam from the sample path and from the reference path to the detector; a means for selecting an appropriate integration time required for adequate detector response; and a means for correlating a detector response, from the sample path relative to a detector response from the reference path, to a quantity of $HbA_{1c}$ or Hb, as appropriate, in said sample.

The apparatus further comprises a quartz-tungsten-halogen bulb capable of emitting a near infrared light beam having wavelengths from 600 nm to 1100 nm and a single optical fiber bundle which randomly samples light from the quartz-tungsten-halogen bulb. The single fiber bundle bifurcates into a sample path beam for travel along a sample path and a reference path beam for travel along a reference path. The bifurcated optical fiber consists of multiple fibers which focus random sampling of light from the lamp, into single fibers of 0.4 millimeter diameter for both the sample and reference beams. This apparatus further comprises two shutters, installed in the lamp assembly, for selectively blocking the sample path light beam which travels along the sample path through a sample enclosed in a housing and the reference path light beam which travels along the reference path. The two light paths are collected into two fibers which converge into a single fiber which is focused onto the detector; the bifurcated collection optical fiber consists of multiple fibers. This apparatus further comprises a grating for dispersing the combined beam into component wavelengths which are passed onto the detector. The detector of this apparatus is a silicon PDA comprised of a plurality of pixels wherein each of the pixels is set to measure one of a plurality of predetermined light frequencies. Based on the measurement of the frequencies, the detector generates a plurality of signals wherein each of the signals is responsive to an amount of radiation received by each of the pixels. This apparatus further comprises an analog-to-digital converter to generate digital information from the plurality of signals and a microprocessor, which is connected to the converter, to correlate the digital information to a quantity of a known substance in the sample.

Alternatively, an InGaAs (Indium-Gallium-Arsenide) PDA which covers the wavelength range of 800 nm to 1700 nm or 1200 nm to 2600 nm can be used, or any commercially available scanning near infrared spectrophotometers which covers the range of 700 nm to 2500 nm.

In another aspect of the invention, a light-tight sample housing is not required. The only shutters in the apparatus are the two located in the lamp assembly, and are used for sequentially directing the light through the sample or reference pathway. Since there is no shutter between the sample housing and the sensor, any room light leakage into the sample housing will affect the sample light and sample dark scans equally when performed at the same integration tie, and also the reference light and reference dark scans when performed at the same integration time used for the reference measurements. Therefore, room light impinging on the detector can be effectively subtracted without affecting the performance of the apparatus, provided that the ambient light does not change during the few seconds measurement time. The room light leakage along sides of the tab, can be managed by measuring the dark current, i.e., detector response when detector is not exposed to the instrument light, for both the sample and reference measurements.

The PDA integrates the optical radiation over a specified time and converts the optical signal to a time multiplexed analog electronic signal called a scan where absorbance is calculated as:

$$\text{Absorbance}_i = \log\{(\text{Reference Light}_i - \text{Reference Dark}_i)/(\text{Sample}$$

$$\text{Light}_i - \text{Sample Dark}_{(i)} + log(ITS/ITR)$$

where

Absorbance$_i$=Absorbance pixel i

Reference Light$_i$=Reference pixel i readings, with reference path open and sample path closed by a shutter;

Reference Dark$_i$=Reference pixel i readings, with reference and sample paths closed by shutters;

Sample Light$_i$=Sample pixel i readings, with sample path open and reference path closed by a shutter;

Sample Dark$_i$=Sample pixel i readings, with sample and reference paths closed by shutters;

ITS=Integration time for sample measurement;

ITR=Integration time for reference measurement; and i=the particular pixel (wavelength) in the PDA.

The electronic signal is proportional to the time that the detector integrates the optical signal. The electronic signal is amplified by analog electronic amplifiers and converted to a digital signal by an analog-to-digital converter or ADC. The digital information from the converter is interpreted for data analysis by a microprocessor which is in turn connected via an RS232 connector to a computer. The results of the data analysis can be displayed on the computer, or on a printer connected.

The integration time for the sample beam is low for a sample with low hematocrit, since there is less scattered light and therefore more light is transmitted to the detector. When the light is sufficiently scattered by, for example a high hematocrit, the spectrophotometer will automatically switch to a higher integration time. The higher integration time chosen will be within a pre-selected range, such that the detector's response is optimal. This feature will allow all samples, from the lowest to the highest hematocrit, to be efficiently tested without exceeding the linear response range of the detector.

Sample Tab

According to another aspect of the present invention, there is provided a sample tab for use in monitoring a diabetic patient's compliance with their insulin dosing regime by spectrophotometry of a blood specimen from the patient, the tab comprising:

a base plate having a top and bottom surface, a well in the top surface, the upper portion of the well being defined by a closed wall extending above the top surface of the plate, at least one notch in the wall to allow drainage of excess blood, and a cover plate, the cover plate and base plate being translucent where the sample resides in the well to allow radiation to be transmitted through the cover plate, blood specimen and the base plate.

According to a further embodiment, the wall of the well is surrounded by a second closed wall to retain excess blood drained from the well, preferably the cover is attached to the base plate.

Figure 2:
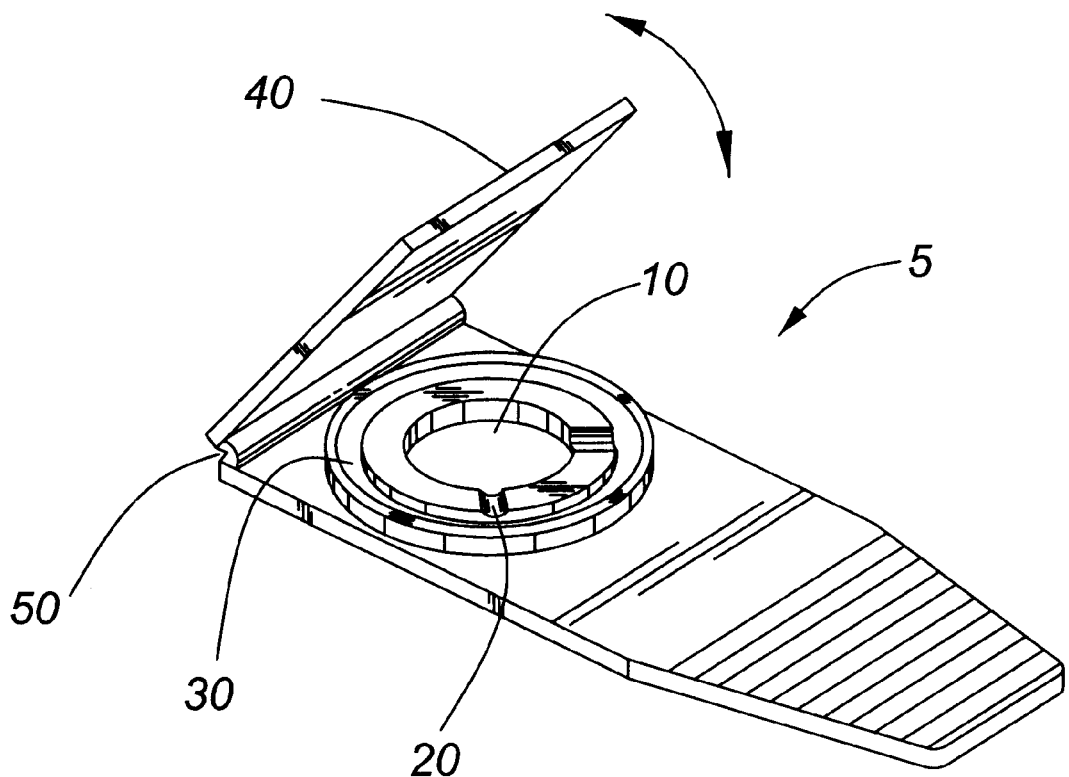
FIG. 2 is a perspective view illustrating the sample tab of the apparatus of FIG. 1.

Referring now to FIG. 2, in a preferred embodiment of a sample tab of the present invention (5), the sample cavity or "well" (10) is 2 millimeter deep and 4 millimeters diameter, i.e., of sufficient size to allow a drop of blood fill the sample cavity, with some excess. Small overflow grooves (20) allow excess blood to flow out of the well. An overflow ring (30) retains any overflow blood from running off the tab. The cover (40) is in a preferred embodiment attached to the tab by a hinge (50). The entire tab may be conveniently manufactured from any suitable plastic material. In the prototype, black plastic washers wit 2-centimeter internal diameter and 2-millimeter thickness were glued to microscope slides, and microscope coverslips were used to cover the samples. Also, a microscope was used as the sample housing after the following modification: the input fiber was sent through the condenser position, and the output fiber was sent through the objective lens; both the condenser and objective were replaced with machined fixtures which housed the ends of the fibres. A microscope stage was used for holding and positioning the slide. For the prototype, 350 $\mu$L of whole blood was used; for the preferred embodiment, 25 $\mu$L would be sufficient. However, the volume of the sample cavity should not be a restriction for the present invention.

The tabs and coverslips can be made of glass as used in microscopy, but plastic is preferred. The plastic can be transparent or translucent. A preferred plastic is polypropylene, which is translucent.

By virtue of the orientation of the sample housing (80), the projection of light is in the vertical direction. An advantage of this is that the red blood cells will remain m the light path, even as they fall downwards under the effect of gravity. It will be obvious to those skilled in the art, that a flow-through cuvette lie those in CO-oximeters can also be used.

Calibration

As with any quantitative method, calibration of the spectrophotometer is required. However the methods for NIR calibration is much more complex than most which can be calibrated with a minimum of a single standard material of known concentration. In respect of NIR calibration, samples must contain all spectral variability expected during the analysis of an unknown sample; the sample must contain an even distribution of the analyte of interest, and the concentrations of total Hb should not correlate significantly with HbA$_{1c}$. The development of the algorithm uses PLS (Partial Least Squares) analysis of the full spectrum. A sample size of several hundred samples is necessary to characterize all the sample variability, particularly due to the various Hb species.

The three parameters measured are grams/liter total hemoglobin (Hb), grams/liter HbA$_{1c}$, and %HbA$_{1c}$. Because % HbA$_{1c}$ is a ratio of HbA$_{1c}$ to total Hb multiplied by 100, % HbA$_{1c}$ is not affected by artifactual dilution caused by instial fluids squeezed out with the blood, when the finger is "milked" for the blood. Similarly, the imprecision in the manufacture of the tabs, in particular with respect to path length, will not affect the % HbA$_{1c}$.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims

We claim:

1. A method of determining a diabetic patient's compliance with their insulin dosing regime comprising:

(i) obtaining an untreated blood specimen from said patient;

(ii) measuring with a spectrophotometer, absorbance of radiation by each of HbA$_{1c}$ and total Hb in said specimen, the radiation being directed into said specimen in a direction that is substantially parallel to the direction in which red blood cells in said specimen fall under the effect of gravity;

(iii) using a calibration algorithm for each of said HbA$_{1c}$ and total Hb to calculate a concentration of each of said HbA$_{1c}$ and total Hb in said specimen from said absorbances measured in step (ii); and (iv) determining a ratio between the concentrations of $HbA_{1c}$ and total Hb, wherein an elevated concentration ratio of $HbA_{1c}$ to total Hb reflects a lack of patient compliance.

2. The method of claim 1, wherein said step of using (step iii), includes a step for calculating a first derivative of at least two portions of a spectrum generated from an absorbance scan for each of $HbA_{1c}$ and total Hb.

3. The method of claim 1, wherein said spectrophotometer measures reflectance instead of absorbance.

4. The method of claim 1, wherein prior to said step of measuring (step ii), said specimen is placed into a sample tab, and the sample tab is inserted into said spectrophotometer, wherein said sample tab comprises a well in which the specimen resides and a cover which closes over the well, and wherein said sample tab is transparent or translucent.

5. A method of determining a diabetic patient's compliance with their insulin dosing regime comprising:
(i) generating a calibration algorithm for each of $HbA_{1c}$ and total Hb;
(ii) obtaining an untreated blood specimen from said patient;
(iii) measuring with a spectrophotometer, absorbance of radiation by each of $HbA_{1c}$ and total Hb in said specimen, the radiation being directed into said specimen in a direction that is substantially parallel to the direction in which red blood cells in said specimen fall under the effect of gravity;
(iv) using said calibration algorithms generated in step (i) to calculate a concentration of each of said $HbA_{1c}$ and total Hb in said specimen from said absorbances measured in step (iii); and
(v) determining a ratio between the concentrations of $HbA_{1c}$ and total Hb, wherein an elevated concentration ratio of $HbA_{1c}$ to total Hb reflects a lack of patient compliance.

6. The method of claim 5, wherein said step of using (step iv), includes a step for calculating a first derivative of at least two portions of a spectrum generated from an absorbance scan for each of $HbA_{1c}$ and total Hb.

7. The method of claim 5, wherein said spectrophotometer measures reflectance instead of absorbance.

8. The method of claim 5, wherein prior to said step of measuring (step iii), said specimen is placed into a sample tab, and the sample tab is inserted into said spectrophotometer, wherein said sample tab comprises a well in which the specimen resides and a cover which closes over the well, and wherein said sample tab is transparent or translucent.

9. A method of assessing the control of diabetes in a patient comprising:
(i) obtaining an untreated blood specimen from said patient;
(ii) measuring with a spectrophotometer, absorbance of radiation by each of $HbA_{1c}$ and total Hb in said specimen, the radiation being directed into said specimen in a direction that is substantially parallel to the direction in which red blood cells in said specimen fall under the effect of gravity;
(iii) using a calibration algorithm for each of said $HbA_{1c}$ and total Hb to calculate a concentration of each of said $HbA_{1c}$ and total Hb in said specimen from said absorbances measured in step (ii); and
(iv) determining a ratio between the concentrations of $HbA_{1c}$ and total Hb, wherein an elevated concentration ratio of $HbA_{1c}$ to total Hb reflects a lack of control of diabetes.

10. The method of claim 9, wherein said step of using (step iii), includes a step for calculating a first derivative of at least two portions of a spectrum generated from an absorbance scan for each of $HbA_{1c}$ and total Hb.

11. The method of claim 9, wherein said spectrophotometer measures reflectance instead of absorbance.

12. The method of claim 9, wherein said diabetes is Type 1 or Type 2 diabetes.

13. The method of claim 9, wherein prior to said step of measuring (step ii), said specimen is placed into a sample tab, and the sample tab is inserted into said spectrophotometer, wherein said sample tab comprises a well in which the specimen resides and a cover which closes over the well, and wherein said sample tab is transparent or translucent.

14. A method of assessing the control of diabetes in a patient comprising:
(i) obtaining an untreated blood specimen from said patient;
(ii) measuring with a spectrophotometer, absorbance of radiation by each of $HbA_{1c}$ and total Hb in said specimen, the radiation being directed into said specimen in a direction that is substantially parallel to the direction in which red blood cells in said specimen fall under the effect of gravity; and
(iii) using a calibration algorithm to calculate a concentration ratio of said $HbA_{1c}$ to total Hb in said specimen from said absorbances measured in step (ii), wherein an elevated ratio of $HbA_{1c}$ to total Hb reflects a lack of control of diabetes.

15. The method of claim 14, wherein said step of using (step iii), includes a step for calculating a first derivative of at least two portions of a spectrum generated from an absorbance scan for each of $HbA_{1c}$ and total Hb.

16. The method of claim 14, wherein said spectrophotometer measures reflectance instead of absorbance.

17. The method of claim 14, wherein said diabetes is Type 1 or Type 2 diabetes.

18. The method of claim 14, wherein prior to said step of measuring (step ii), said specimen is placed into a sample tab, and the sample tab is inserted into said spectrophotometer, wherein said sample tab comprises a well in which the specimen resides and a cover which closes over the well, and wherein said sample tab is transparent or translucent.

19. A method of assessing the control of diabetes in a patient comprising:
(i) generating a calibration algorithm for each of $HbA_{1c}$ and total Hb;
(ii) obtaining an untreated blood specimen from said patient;
(iii) measuring with a spectrophotometer, absorbance of radiation by each of $HbA_{1c}$ and total Hb in said specimen, the radiation being directed into said specimen in a direction that is substantially parallel to the direction in which red blood cells in said specimen fall under the effect of gravity;
(iv) using said calibration algorithms generated in step (i) to calculate a concentration of each of said $HbA_{1c}$ and total Hb in said specimen from said absorbances measured in step (iii); and (v) determining a ratio between the concentrations of $HbA_{1c}$ and total Hb, wherein an elevated concentration ratio of $HbA_{1c}$ to total Hb reflects a lack of control of diabetes.

20. The method of claim 19, wherein said step of using (step iv), includes a step for calculating a first derivative of at least two portions of a spectrum generated from an absorbance scan for each of $HbA_{1c}$ and total Hb.

21. The method of claim 19, wherein said spectrophotometer measures reflectance instead of absorbance.

22. The method of claim 19, wherein said diabetes is Type 1 or Type 2 diabetes.

23. The method of claim 19, wherein prior to said step of measuring (step iii), said specimen is placed into a sample tab, and the sample tab is inserted into said spectrophotometer, wherein said sample tab comprises a well in which the specimen resides and a cover which closes over the well, and wherein said sample tab is transparent or translucent.

24. A method of assessing the control of diabetes in a patient comprising:

(i) generating a calibration algorithm for both of $HbA_{1c}$ and total Hb;

(ii) obtaining an untreated blood specimen from said patient;

(iii) measuring with a spectrophotometer, absorbance of radiation by each of $HbA_{1c}$ and total Hb in said specimen, the radiation being directed into said specimen in a direction that is substantially parallel to the direction in which red blood cells in said specimen fall under the effect of gravity; and (iv) using said calibration algorithms to calculate a concentration ratio of said $HbA_{1c}$ to total Hb in said specimen from said absorbances measured in step (iii), wherein an elevated concentration ratio of $HbA_{1c}$ to total Hb reflects a lack of control of diabetes.

25. The method of claim 24, wherein said step of using (step iv), includes a step for calculating a first derivative of at least two portions of a spectrum generated from an absorbance scan for each of $HbA_{1c}$ and total Hb.

26. The method of claim 24, wherein said spectrophotometer measures reflectance instead of absorbance.

27. The method of claim 24, wherein said diabetes is Type 1 or Type 2 diabetes.

28. The method of claim 24, wherein prior to said step of measuring (step iii), said specimen is placed into a sample tab, and the sample tab is inserted into said spectrophotometer, wherein said sample tab comprises a well in which the specimen resides and a cover which closes over the well, and wherein said sample tab is transparent or translucent.

* * * * *

UNITED STATES PATENT AND TRADEMARK OFFICE
CERTIFICATE OF CORRECTION

PATENT NO.     : 6,582,964 B1                                          Page 1 of 1
DATED          : June 24, 2003
INVENTOR(S)    : James Samsoondar et al.

It is certified that error appears in the above-identified patent and that said Letters Patent is hereby corrected as shown below:

<u>Title page,</u>
Item [75], Inventors, please change the name of the third listed inventor to correctly read: -- Borge Petersen, Elimira (CA) --

Signed and Sealed this

Sixteenth Day of September, 2003

JAMES E. ROGAN
*Director of the United States Patent and Trademark Office*